(12) United States Patent
LeMay et al.

(10) Patent No.: US 8,197,434 B2
(45) Date of Patent: Jun. 12, 2012

(54) TAMPON ASSEMBLY HAVING SHAPED PLEDGET

(75) Inventors: Jessica E. LeMay, New York, NY (US); Patrick Gorham, Wyoming, DE (US); Keith Edgett, Middletown, DE (US); George Jarmon, Camden/Wyoming, DE (US)

(73) Assignee: Playtex Products, Inc., Westport, CT (US)

( * ) Notice: Subject to any disclaimer, the term of this patent is extended or adjusted under 35 U.S.C. 154(b) by 471 days.

(21) Appl. No.: 10/834,386

(22) Filed: Apr. 28, 2004

(65) Prior Publication Data

US 2004/0243088 A1 Dec. 2, 2004

Related U.S. Application Data

(60) Provisional application No. 60/467,482, filed on May 2, 2003.

(51) Int. Cl.
*A61F 13/20* (2006.01)

(52) U.S. Cl. ............................ 604/15; 604/11

(58) Field of Classification Search ............... D24/125, D24/141; 28/118–120; 604/904, 385.17, 604/385.18, 285, 286, 11–18, 354, 59, 60
See application file for complete search history.

(56) References Cited

U.S. PATENT DOCUMENTS

| | | | |
|---|---|---|---|
| 1,555,708 A | 9/1925 | Gale | |
| 1,731,665 A | 10/1929 | Huebsch | |
| 2,077,231 A | 4/1937 | Fourness et al. | |
| 2,095,377 A | 10/1937 | Breese | |
| 2,099,931 A | 11/1937 | Fourness | |
| 2,123,750 A | 7/1938 | Schulz | |
| 2,178,704 A | 11/1939 | Robinson | |
| 2,254,272 A | 9/1941 | Crockford | |
| 2,301,868 A | 11/1942 | Gurley, Jr. et al. | |
| 2,306,406 A | 12/1942 | Robinson | |
| 2,386,590 A | 10/1945 | Calhoun | |
| 2,499,414 A | 3/1950 | Rabell | |
| 2,799,055 A | 7/1957 | Carrier | |
| 2,854,978 A | 10/1958 | Millman et al. | |
| 2,905,175 A | 9/1959 | Schwartz | |
| 3,291,130 A | 12/1966 | Whitehead | |
| 3,306,294 A | 2/1967 | Penksa | |

(Continued)

FOREIGN PATENT DOCUMENTS

DE 3328910 2/1985

(Continued)

OTHER PUBLICATIONS

Photocopy of box panels for O.B. Silk Ease, Personal Fit Protection.

(Continued)

*Primary Examiner* — Lynne Anderson
(74) *Attorney, Agent, or Firm* — Ohlandt, Greeley, Ruggiero & Perle, LLP

(57) ABSTRACT

A tampon assembly having a barrel, a plunger, and a pledget is provided. The plunger is slidably received in the barrel. The pledget is in the barrel between the insertion tip and the plunger so that a force applied on the plunger can expel the pledget from the barrel. The barrel has a plurality of petals defining an insertion tip, which has a first taper ratio of more than about 0.3 to less than 1.0. The pledget has a shaped tip that is disposed in the insertion tip.

15 Claims, 4 Drawing Sheets

U.S. PATENT DOCUMENTS

| | | | |
|---|---|---|---|
| 3,306,295 A | 2/1967 | Penksa | |
| 3,369,544 A | 2/1968 | Crockford | |
| 3,397,695 A | 8/1968 | Voss | |
| 3,431,909 A | 3/1969 | Krusko | |
| 3,431,910 A | 3/1969 | Kokx | |
| 3,520,302 A | 7/1970 | Jones | |
| 3,570,489 A | 3/1971 | Brown | |
| 3,572,341 A | 3/1971 | Glassman | |
| 3,595,236 A | 7/1971 | Corrigan | |
| 3,643,661 A | 2/1972 | Crockford | |
| 3,683,915 A | 8/1972 | Voss | |
| 3,690,321 A | 9/1972 | Hirschman | |
| 3,695,270 A | 10/1972 | Dostal | |
| 3,706,311 A | 12/1972 | Kokx et al. | |
| 3,710,793 A | 1/1973 | Glassman | |
| 3,712,305 A | 1/1973 | Wennerblom et al. | |
| 3,726,277 A | 4/1973 | Hirschman | |
| 3,731,687 A | 5/1973 | Glassman | |
| 3,738,364 A | 6/1973 | Brien et al. | |
| 3,762,413 A | 10/1973 | Hanke | |
| 3,794,029 A | 2/1974 | Dulle | |
| 3,812,856 A | 5/1974 | Duncan et al. | |
| 3,834,389 A | 9/1974 | Dulle | |
| 3,845,767 A | 11/1974 | Friese et al. | |
| 3,856,013 A | 12/1974 | Dulle | |
| 3,858,571 A | 1/1975 | Rudolph | |
| 3,885,563 A | 5/1975 | Johnson et al. | |
| 3,905,372 A | 9/1975 | Denkinger | |
| 3,946,737 A | 3/1976 | Kobler | |
| 3,971,378 A | 7/1976 | Krantz | |
| 3,981,305 A | 9/1976 | Ring | |
| 3,983,873 A | 10/1976 | Hirschman | |
| 3,994,298 A | 11/1976 | Des Marais | |
| 4,010,751 A | 3/1977 | Ring | |
| 4,018,255 A | 4/1977 | Diggs | |
| 4,027,673 A | 6/1977 | Poncy et al. | |
| 4,077,408 A | 3/1978 | Murray et al. | |
| 4,077,409 A | 3/1978 | Murray et al. | |
| 4,108,180 A | 8/1978 | Moehrle | |
| D250,663 S * | 12/1978 | Koch et al. | D24/141 |
| 4,175,467 A | 11/1979 | Lashley | |
| 4,185,631 A | 1/1980 | McConnell | |
| 4,211,225 A | 7/1980 | Sibalis | |
| 4,212,301 A | 7/1980 | Johnson | |
| 4,217,900 A | 8/1980 | Wiegner et al. | |
| 4,266,546 A | 5/1981 | Roland et al. | |
| 4,274,412 A | 6/1981 | Austin | |
| 4,278,088 A | 7/1981 | Reeves et al. | |
| 4,291,696 A | 9/1981 | Ring | |
| 4,294,253 A | 10/1981 | Friese | |
| 4,308,867 A | 1/1982 | Roseman et al. | |
| 4,309,997 A | 1/1982 | Donald | |
| 4,312,348 A | 1/1982 | Friese | |
| 4,318,407 A | 3/1982 | Woon | |
| 4,328,804 A | 5/1982 | Shimatani | |
| 4,335,720 A | 6/1982 | Glassman | |
| 4,335,721 A | 6/1982 | Matthews | |
| 4,341,214 A | 7/1982 | Fries et al. | |
| 4,351,339 A | 9/1982 | Sneider | |
| 4,361,151 A | 11/1982 | Fitzgerald | |
| 4,475,911 A | 10/1984 | Gellert | |
| 4,543,086 A * | 9/1985 | Johnson | 604/11 |
| 4,543,098 A | 9/1985 | Wolfe et al. | |
| 4,553,965 A | 11/1985 | Conn et al. | |
| 4,743,237 A | 5/1988 | Sweere | |
| 4,755,166 A | 7/1988 | Olmstead | |
| 4,845,922 A | 7/1989 | Sweere | |
| 5,019,061 A | 5/1991 | Hoden et al. | |
| 5,047,024 A | 9/1991 | Glassman | |
| 5,084,038 A | 1/1992 | Sheldon et al. | |
| 5,112,348 A | 5/1992 | Glassman | |
| 5,153,971 A | 10/1992 | Van Iten | |
| 5,158,535 A | 10/1992 | Paul et al. | |
| 5,267,953 A | 12/1993 | Paul et al. | |
| 5,342,331 A | 8/1994 | Silber et al. | |
| 5,350,371 A | 9/1994 | Van Iten | |
| 5,370,633 A | 12/1994 | Villalta | |
| 5,387,206 A | 2/1995 | Valentine et al. | |
| 5,395,308 A | 3/1995 | Fox et al. | |
| 5,403,300 A | 4/1995 | Howarth | |
| 5,417,224 A | 5/1995 | Petrus et al. | |
| 5,437,628 A | 8/1995 | Fox et al. | |
| 5,445,605 A | 8/1995 | Plüss | |
| 5,542,914 A | 8/1996 | Van Iten | |
| 5,554,108 A | 9/1996 | Browning et al. | |
| 5,584,827 A | 12/1996 | Korteweg et al. | |
| 5,592,725 A | 1/1997 | Brinker | |
| 5,634,248 A | 6/1997 | McNelis et al. | |
| 5,659,934 A | 8/1997 | Jessup et al. | |
| 5,683,358 A * | 11/1997 | Nielsen et al. | 604/11 |
| 5,718,675 A | 2/1998 | Leijd | |
| 5,738,646 A * | 4/1998 | Fox et al. | 604/15 |
| 5,755,906 A | 5/1998 | Achter et al. | |
| 5,772,645 A | 6/1998 | Zadini et al. | |
| 5,792,096 A * | 8/1998 | Rentmeester et al. | 604/14 |
| 5,795,346 A | 8/1998 | Achter et al. | |
| 5,800,338 A | 9/1998 | Kollerup et al. | |
| 5,807,372 A | 9/1998 | Balzar | |
| 5,817,047 A | 10/1998 | Osborn, III et al. | |
| 5,827,251 A | 10/1998 | Moder et al. | |
| 5,873,971 A | 2/1999 | Balzar | |
| 5,891,127 A | 4/1999 | Moder et al. | |
| 5,911,712 A | 6/1999 | Leutwyler et al. | |
| 5,928,184 A | 7/1999 | Etheredge et al. | |
| 5,947,992 A | 9/1999 | Zadini et al. | |
| 5,964,741 A | 10/1999 | Moder et al. | |
| 5,986,165 A | 11/1999 | Moder et al. | |
| 6,003,216 A | 12/1999 | Hull, Jr. et al. | |
| 6,039,716 A | 3/2000 | Jessup et al. | |
| 6,039,828 A | 3/2000 | Achter et al. | |
| 6,068,899 A | 5/2000 | Osborn, III et al. | |
| 6,071,259 A | 6/2000 | Steiger et al. | |
| 6,090,038 A | 7/2000 | Zunker et al. | |
| 6,142,928 A | 11/2000 | Zunker et al. | |
| 6,177,606 B1 | 1/2001 | Etheredge et al. | |
| 6,177,608 B1 | 1/2001 | Weinstrauch | |
| 6,180,051 B1 | 1/2001 | Schoelling | |
| 6,183,436 B1 | 2/2001 | Korteweg et al. | |
| 6,191,341 B1 | 2/2001 | Shippert | |
| 6,206,867 B1 | 3/2001 | Osborn, III et al. | |
| 6,254,566 B1 | 7/2001 | Buck et al. | |
| 6,270,470 B1 | 8/2001 | Buck et al. | |
| 6,283,952 B1 | 9/2001 | Child et al. | |
| 6,299,573 B1 | 10/2001 | Hull, Jr. et al. | |
| 6,302,861 B2 | 10/2001 | Tweddell, III et al. | |
| 6,302,862 B1 | 10/2001 | Osborn, III et al. | |
| 6,310,269 B1 | 10/2001 | Friese et al. | |
| 6,358,235 B1 | 3/2002 | Osborn, III et al. | |
| 6,380,455 B1 | 4/2002 | Moder et al. | |
| 6,419,777 B1 | 7/2002 | Achter et al. | |
| 6,432,246 B1 | 8/2002 | Blake | |
| 6,465,713 B1 | 10/2002 | Gell et al. | |
| 6,478,764 B1 * | 11/2002 | Suga | 604/15 |
| 6,508,780 B1 * | 1/2003 | Edgett et al. | 604/15 |
| 6,570,052 B2 | 5/2003 | Zadini et al. | |
| D477,075 S | 7/2003 | Schoelling | |
| 6,585,300 B1 | 7/2003 | Rajala et al. | |
| 6,645,136 B1 | 11/2003 | Zunker et al. | |
| 6,654,992 B2 | 12/2003 | Rajala et al. | |
| 2002/0107497 A1 | 8/2002 | Osborn et al. | |
| 2002/0133135 A1 | 9/2002 | Gell et al. | |
| 2002/0143303 A1 | 10/2002 | Intravartolo et al. | |
| 2002/0147436 A1 | 10/2002 | Gell et al. | |
| 2002/0151859 A1 | 10/2002 | Schoelling | |
| 2002/0177835 A1 | 11/2002 | Zadini et al. | |
| 2003/0055391 A1 | 3/2003 | Nguyen et al. | |
| 2003/0125658 A1 | 7/2003 | Marvin | |
| 2003/0130637 A1 | 7/2003 | Intravartolo et al. | |
| 2003/0135180 A1 | 7/2003 | Nguyen et al. | |
| 2003/0167048 A1 | 9/2003 | Policappelli | |
| 2003/0172504 A1 | 9/2003 | Sageser et al. | |
| 2003/0176844 A1 | 9/2003 | Randall et al. | |
| 2003/0176845 A1 | 9/2003 | Kollwitz et al. | |
| 2003/0208179 A1 | 11/2003 | Fuchs et al. | |
| 2003/0208180 A1 | 11/2003 | Fuchs et al. | |
| 2004/0054317 A1 * | 3/2004 | Lemay et al. | 604/15 |
| 2004/0064082 A1 | 4/2004 | LeMay | 604/368 |

| | | | | | |
|---|---|---|---|---|---|
| 2004/0199100 A1 | 10/2004 | LeMay et al. .................. 604/11 | WO | WO 94/15564 | 7/1994 |
| 2004/0199102 A1* | 10/2004 | LeMay et al. .................. 604/11 | WO | WO 2004/098449 A2 | 11/2004 |
| 2005/0070645 A1 | 3/2005 | Williams ................. 264/328.17 | WO | WO 2004/098449 A3 * | 11/2006 |

FOREIGN PATENT DOCUMENTS

| | | |
|---|---|---|
| DE | 3609852 | 9/1987 |
| DE | 3726311 | 2/1989 |
| DE | 4446226 | 6/1995 |
| DE | 19726648 | 12/1998 |
| DE | 19747633 | 3/1999 |
| EP | 110793 | 12/1983 |
| EP | 158543 | 3/1985 |
| EP | 546256 | 7/1992 |
| EP | 797971 | 10/1997 |
| FR | 2567399 | 7/1984 |
| JP | 55-179096 | 12/1980 |
| JP | 5212073 | 8/1993 |
| JP | 10024064 | 1/1998 |
| JP | 2000288018 | 10/2000 |
| JP | 200117465 | 1/2001 |
| JP | 2001-145658 | 5/2001 |
| JP | 2005-531345 | 10/2005 |
| WO | WO 93/08779 | 5/1993 |

OTHER PUBLICATIONS

Australian Examiner's First Report on Patent Application No. 2008223372 dated Aug. 10, 2010.
European Search Report dated Apr. 27, 2011 for corresponding European Patent Application No. 04760601.7.
Israeli Office Action for corresponding Israeli Patent Application No. 200734 with English summary dated Apr. 5, 2011.
Examination Report dated Aug. 25, 2011 from corresponding European Application No. 04 760 601.7-1217.
Office Action dated Apr. 6, 2011 for corresponding Canadian Patent Application No. 2,680,144.
Office Action dated Jun. 14, 2011 from Korean Patent Application No. 10-2009-7020746.
Notice of Reasons for Rejection dated Feb. 20, 2012 from Japanese Application No. 2009-552722.
Official Notice of Final Rejection dated Feb. 27, 2012 from Korean Application No. 10-2009-7020746.

* cited by examiner

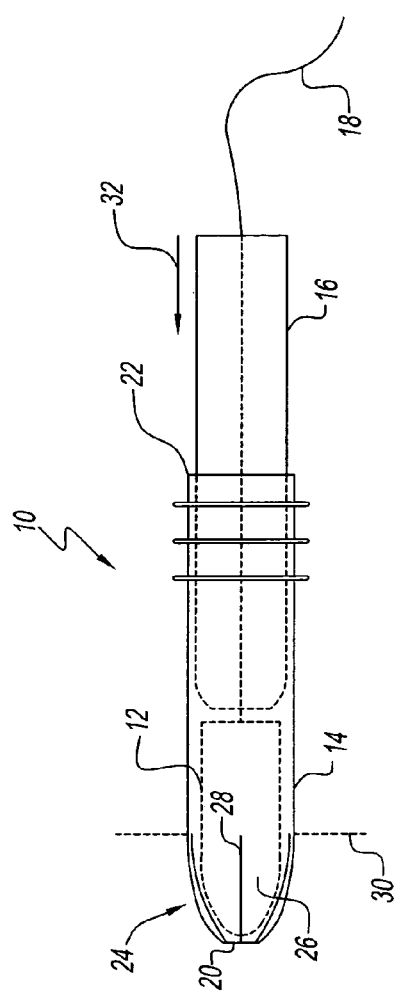
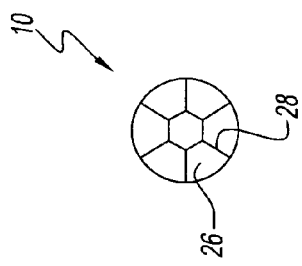
Fig. 1
Fig. 2

TAMPON ASSEMBLY HAVING SHAPED PLEDGET

CROSS REFERENCE TO RELATED APPLICATIONS

This application claims the benefit of U.S. Provisional Application Ser. No. 60/467,482, filed May 2, 2003 the contents of which are incorporated by reference herein.

BACKGROUND OF THE INVENTION

1. Field of the Invention

The present invention is related to a tampon assembly. More particularly, the present invention is related to a tampon assembly that has a shaped pledget.

2. Description of Related Art

A tampon assembly is used to inject an absorbent or hygienic material, known as a tampon pledget, into the vaginal vault. The pledget of commercial tampon assemblies is typically positioned in a barrel for expulsion from a barrel by a plunger. The use of such assemblies requires a user to insert an end of the barrel into the vaginal vault.

Once the barrel has been inserted, the plunger can be used to expel the pledget from the end of the barrel into the vaginal vault. Once the pledget is in position, the pledget expands upon contact with moisture to conform to contours of the body and, thus, provide leakage protection. Comfort to the user during insertion of the barrel and expulsion of the pledget is an important aspect for the commercial success of the tampon assembly.

Many attempts have been made to increase the comfort associated with the use of tampon assemblies. For example, the barrel of some tampon assemblies include a dome shaped end. The dome shaped end includes a number or plurality of shaped petals configured to open during expulsion of the pledget. Unfortunately, the petals themselves can be a source of discomfort. For example, the petals can collapse during insertion of the barrel, which can increase the force required to eject the pledget from the barrel. This has led prior assemblies to increase the thickness of the petals to prevent the petals from collapsing. However, the increased petal thickness can also increase the force required to eject the pledget from the barrel. Since increases in ejection force can result in the applicator being difficult to use, neither solution has been desirable.

Accordingly, there is a continuing need for tampon assemblies that can increase comfort by addressing one or more of the aforementioned drawbacks and deficiencies.

BRIEF SUMMARY OF THE INVENTION

It is an object of the present invention to provide a tampon assembly having a shaped pledget.

It is another object to provide a tampon assembly having a tapered insertion tip that has its inside surface supported by a shaped pledget.

It is yet another object to provide a tampon assembly that has an applicator barrel that is easy to insert, and a shaped pledget that gradually opens the petals of the barrel.

These and other objects of the present invention are provided by a tampon assembly having a barrel, a plunger, and a pledget. The plunger is slidably received in the barrel. The pledget is in the barrel between the insertion tip and the plunger so that a force applied on the plunger can expel the pledget from the barrel. The barrel has a plurality of petals defining an insertion tip, which has a first taper ratio of more than about 0.3 to less than 1.0. The pledget has a shaped tip that is disposed in the insertion tip.

These and other objects of the present invention are also provided by a tampon assembly having a barrel, a plunger, and a pledget. The barrel has a plurality of petals defining an insertion tip. The insertion tip has an inner surface area. The plunger is slidably received in the barrel. The pledget has a shaped tip. The pledget is in the barrel so that the shaped tip supports a portion of the inner surface area. A force applied to the plunger can expel the pledget from the barrel through the plurality of petals.

The above-described and other features and advantages of the present invention will be appreciated and understood by those skilled in the art from the following detailed description, and drawings.

BRIEF DESCRIPTION OF THE SEVERAL VIEWS OF THE DRAWINGS

FIG. 1 is a side view of an exemplary embodiment of a tampon assembly according to the present invention;

FIG. 2 is an end view of the assembly of FIG. 1;

DETAILED DESCRIPTION OF THE INVENTION

Figure 3:
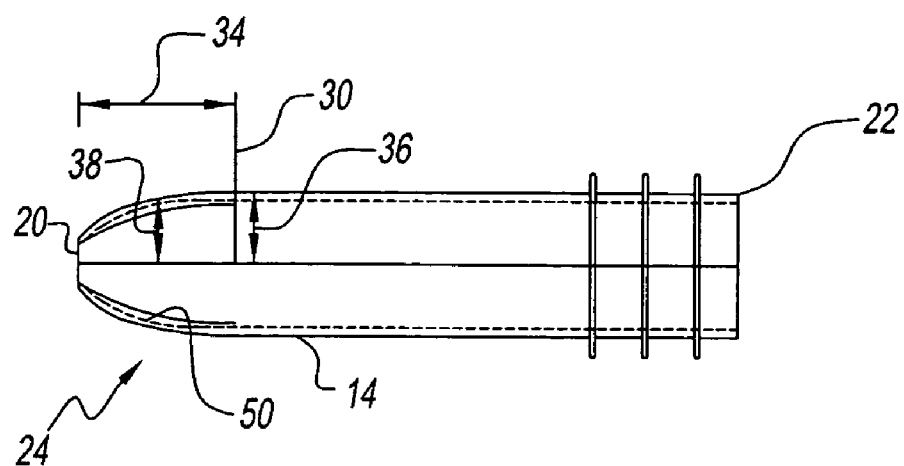
FIG. 3 is a side view of the barrel of FIG. 1.

Referring now to the drawings and more particularly to FIGS. 1 and 2, an exemplary embodiment of a tampon assembly generally represented by reference numeral 10 is illustrated. Assembly 10 has a shaped pledget 12, a barrel 14, and a plunger 16. Pledget 12 can include a withdrawal cord 18 connected thereto, which extends out of assembly 10.

Shaped pledget 12 is disposed in barrel 14 and significantly improves the performance of assembly 10 as compared to prior assemblies having a blunt or squared-off pledget.

Barrel 14 has a first end 20 and a second end 22. First end 20 defines an insertion tip 24 having a number or plurality of petals 26. Petals 26 are defined in first end 20 by a number or plurality of slits 28. Insertion tip 24 terminates at a plane 30 defined at the base or root of petals 26 (e.g., the bottom of slits 28).

Barrel 14 is illustrated by way of example as including six petals 26. Of course, it is contemplated by the present invention for barrel 14 to have more or less than six petals. For example, barrel 14 can have between about two to about eight petals 26.

Plunger 16 is useable to expel pledget 12 from barrel 14. Plunger 16 is slidably disposed in barrel 14 at second end 22. Pledget 12 is expelled through first end 20 through the movement of plunger 16 in the direction of arrow 32. As plunger 16 moves in the direction of arrow 32, the plunger can urge pledget 12 into petals 26 until the petals open along slits 28 and the pledget is expelled from barrel 14 through insertion tip 24.

Referring to FIG. 3, insertion tip 24 has a length 34, an outer radial dimension 36, and an inner radial dimension 38. Preferably, barrel 14 has a minimal thickness such that inner and outer dimensions 36, 38, respectively, can be considered to be substantially similar.

Length 34 is defined as the distance between first end 20 and plane 30. Insertion tip 24 is, preferably, tapered or elliptical in shape. Specifically, dimensions 36, 38 decrease along length 34, linearly or non-linearly, from a maximum at plane 30 to a minimum at first end 20.

The taper of insertion tip 24 is defined as a ratio of the maximum radial dimension of insertion tip 24, namely radial dimension 36 at plane 30, divided by length 34. Preferably, insertion tip 24 has a taper ratio of more than about 0.3 to less than 1.0, preferably about 0.6.

Figure 4:
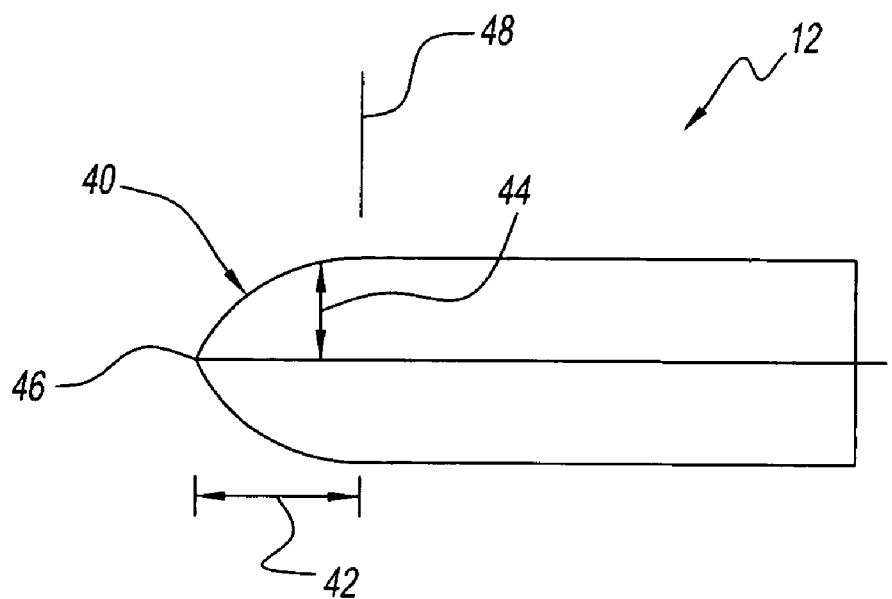
FIG. 4 is a side view of the shaped pledget of FIG. 1.

It has been determined that the perceived and actual level of comfort of assembly 10 can be enhanced through the use of shaped pledget 12, shown in FIG. 4, for supporting petals 26 of insertion tip 24.

Pledget 12 has a tip section 40 that is, preferably, shaped to support insertion tip 24. Tip section 40 has a length 42 and an outer radial dimension 44 that decreases or is tapered along length 42. Length 42 is defined as the distance between a front end 46 of pledget 12 and a plane 48. Plane 48 is defined as a plane through pledget 12 where the taper of tip section 40 begins.

Tip section 40 supports or contacts (hereinafter "supports") an inner surface area 50 of insertion tip 24 to provide increased comfort as compared to prior assemblies. Inner surface area 50 is defined as the surface area of tip 24 between first end 20 and plane 30.

Tip section 40 supports a portion 52 of inner surface area 50. Portion 52 is considered to be "supported" by tip section 40 when outer dimension 44 is at least about 75%, more preferably about 85%, most preferably about 95% of inner dimension 38.

Figure 6:
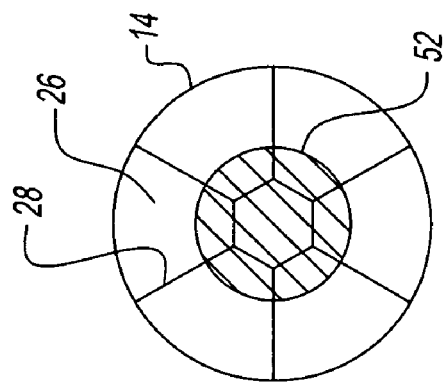
FIG. 6 is a view taken along lines 6-6 in FIG. 5.
Figure 5:
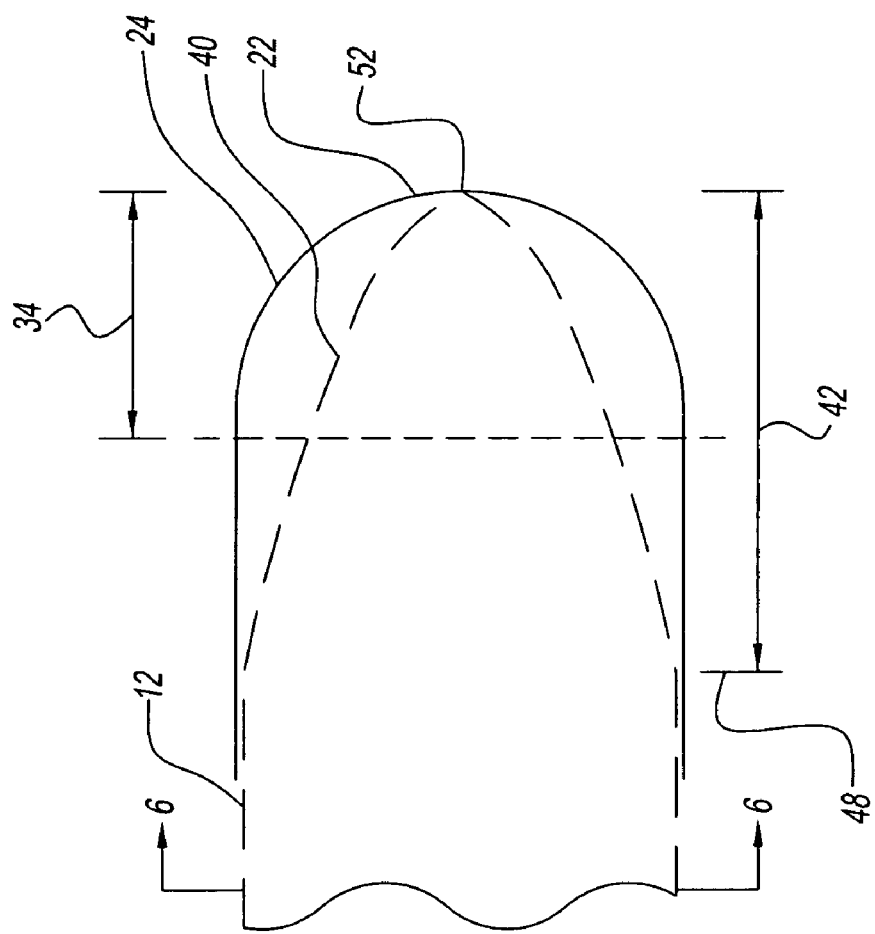
FIG. 5 is an exemplary embodiment of an insertion tip having a shaped pledget according to the present invention.

Referring now to FIGS. 5 and 6, an exemplary embodiment of portion 52 supported by tip section 40 is illustrated. Insertion tip 24 is illustrated having a taper ratio of less than 1.0. Tip section 40 of pledget 12 is illustrated supporting portion 52, which starts at first end 20 and runs along inner surface area 50 towards plane 30. In this embodiment, pledget 12 supports petals 26 at least at first end 20. It is contemplated that portion 52 can support at least about 10%, preferably at least about 50%, most preferably about 100% of surface area 50.

Figure 8:
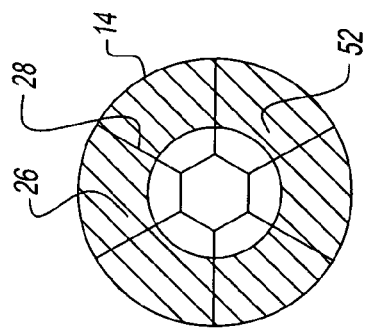
FIG. 8 is a view taken along lines 8-8 in FIG. 7.
Figure 7:
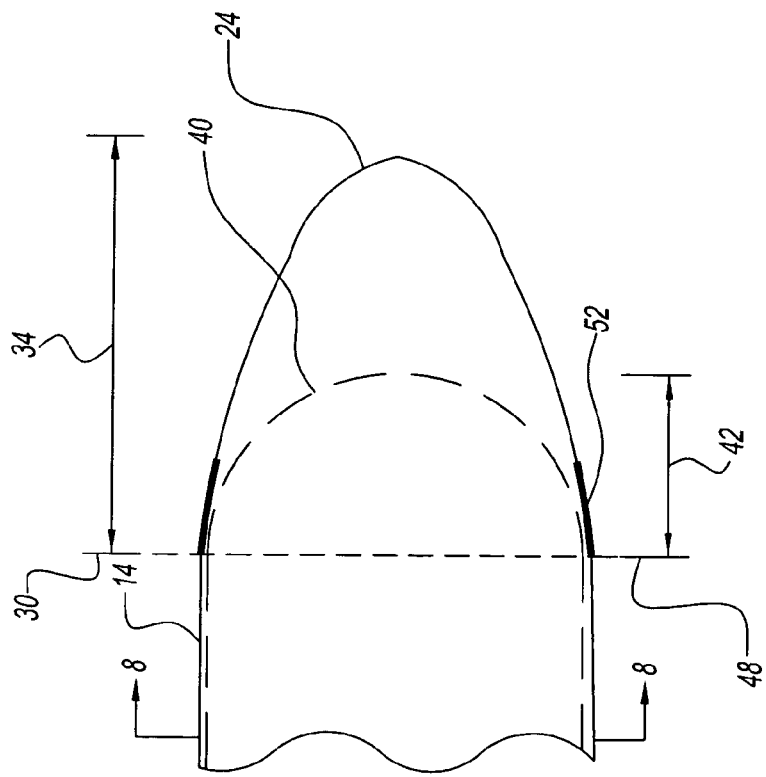
FIG. 7 is an alternate exemplary embodiment of an insertion tip having a shaped pledget.

Referring now to FIGS. 7 and 8, an alternate exemplary embodiment of portion 52 supported by tip section 40 is illustrated. Insertion tip 24 is illustrated having a taper ratio of about 0.7. Tip section 40 of pledget 12 is illustrated supporting portion 52, which starts at plane 30 and runs along inner surface area 50 towards first end 20. In this embodiment, pledget 12 supports petals 26 at least at the base of the petals, namely at least at plane 30. It is contemplated that portion 52 can support at least about 10%, preferably at least about 50%, most preferably about 100% of surface area 50.

Figure 9:
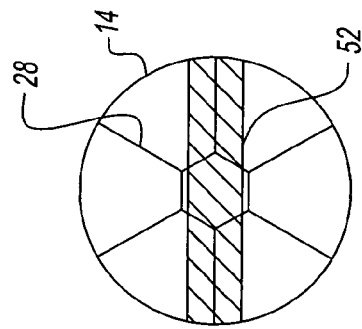
FIG. 9 is an alternate embodiment of the view of FIG. 8.

It should be recognized that portion 52 is illustrated in FIGS. 6 and 8 as being circular. However, it is also contemplated for tip section 40 of pledget 12 to support specific portions 52 of inner surface area 50. For example, portion 52 can support inner surface area 50 at least at slits 28 of petals 26 as illustrated in FIG. 9.

Shaped pledget 12 should, preferably, occupy at least about 50% of the volume of insertion tip 24, more preferably about 75%, most preferably about 95%, where the tip volume is the void defined by petals 26 and plane 30. When pledget 12 has a taper ratio (e.g., dimension 44 divided by dimension 42) that is greater than the taper ratio of insertion tip 24 as in FIG. 7, length 42 of pledget 12 should occupy at least about 50% of length 34 of insertion tip 24, more preferably about 75%, most preferably about 95%. However, when pledget 12 has a taper ratio that is less than the taper ratio of insertion tip 24 as in FIG. 5, dimension 44 of the pledget at any given point along its length 42 should be at least about 50% of the dimension 38 of applicator tip 24 at the corresponding point, more preferably about 75%, most preferably about 95%.

Advantageously, shaped pledget 12 prevents forces on insertion tip 24 applied during insertion of barrel 14 into the body from collapsing petals 26 inward towards the pledget. Further, shaped pledget 12 enables the petals 26 to be made thinner to decrease the expulsion force while stilling mitigating the collapse or deflection of petals 26.

Shaped pledget 12 also has been found to reduce instances of pinching and scratching by petals 26 during insertion of barrel 14. In prior assemblies having blunt or unshaped pledgets, users often push the pledget as far into the applicator tip as possible prior to insertion of the applicator. However, this can cause the petals to open prematurely, namely before insertion of the barrel into the body. The open petals provide prior barrels with a "claw-like" insertion tip, which can scratch during insertion of the barrel. Also, the open petals can close during the insertion process, which can pinch the skin of the user. Since shaped pledget 12 supports surface area 50, assembly 10 mitigates instances of these drawbacks and deficiencies of prior assemblies having an unshaped pledget.

Assembly 10 has been found to increase comfort of use during both the insertion of barrel 14 and the expulsion of pledget 12. First, the taper ratio of insertion tip 24 facilitates insertion comfort by gradually parting the vulva-vaginal channel over a longer length of the barrel as compared to prior blunt ended barrels. In addition, tip section 40 of pledget 12 gradually opens petals 26 over a longer length of the pledget as compared to prior blunt ended pledgets.

Tip section 40 of pledget 12 can be shaped by compressing the tip to a higher density than the rest of the pledget. Alternately, tip section 40 can be shaped providing the tip with a less dense material that, when compressed, provides the tip with the same density as the rest of the pledget. In addition, tip section 40 of pledget 12 can be shaped by cutting or trimming the tip to the desired shape so that the tip has the same density as the rest of the pledget. Of course, combinations of one or more of the aforementioned methods is contemplated by the present invention.

Suitable materials for forming shaped pledget 12 include, for example, cellulosic fibers such as, but not limited to rayon fibers, cotton fibers, pulp fibers, and any combinations thereof.

Suitable materials for forming barrel 14 and/or plunger 16 include, for example, biopolymer, cardboard, heat shrink plastic, paper slurry, plastic, plastic tubing, pulp slurry, pulp-molded paper, or any combinations thereof. By way of example, barrel 14 can be formed of low-density polyethylene (LDPE), and plunger 16 can be formed of axially oriented high-density polyethylene (HDPE). In addition, barrel 14 and/or plunger 16 may be coated with a coating material to reduce friction and/or increase strength. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

It should be recognized that pledget 12, barrel 14, and/or plunger 16 can have any cross-sectional shape, such as circular and non-circular, including oval or polygonal shapes. Furthermore, it is contemplated by the present invention for the cross-sectional shape to vary along the length of pledget 12, barrel 14, and/or plunger 16.

It should also be noted that the terms "first", "second", and "third" and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the disclosure without departing from the scope thereof.

What is claimed is:

1. A tampon assembly comprising:
   a barrel having a tubular wall forming a first end and a second end, said barrel having a plurality of discrete petals at said first end that form an insertion tip, said petals being separated from each other by a plurality of cuts that form a break of material through said tubular wall of said barrel, said petals having an inner surface, said insertion tip being of an axial extant defined from a distal end of said first end to a first plane defined at a base of said plurality of petals, said insertion tip having a first taper ratio of more than about 0.3 to less than 1.0 throughout said axial extant;
   a plunger being slidably received in said barrel; and
   a pledget being disposed in said barrel between said insertion tip and said plunger so that a force applied on said plunger can expel said pledget from said barrel, wherein said pledget has a tapered tip compatible with and proximate said insertion tip, said tapered tip of said pledget having an outer radial dimension that decreases between a distal, tip end of said pledget and a second plane through said pledget where said taper begins, wherein said tapered tip contacts and supports about 100% of said inner surface of said plurality of petals, prior to insertion of the tampon assembly into a body of a user, to prevent forces on said insertion tip applied during insertion from collapsing said plurality of petals inward towards said pledget, whereby the compatibility of said insertion tip of said barrel and said tapered tip of said pledget mitigates against said plurality of petals closing during insertion which closing can pinch a user.

2. The assembly as in claim 1, wherein said tapered tip has a density that is higher than the density of the remainder of said pledget.

3. The assembly as in claim 1, wherein said tapered tip has a density that is substantially equal to the density of the remainder of said pledget.

4. The assembly as in claim 1, wherein said tapered tip has a second taper ratio approximately equal to said first taper ratio.

5. The assembly as in claim 1, wherein said tapered tip has a second taper ratio that is greater than said first taper ratio.

6. The assembly as in claim 1, wherein said tapered tip has a second taper ratio that is less than said first taper ratio.

7. The assembly as in claim 1, wherein said tapered tip occupies about 50% of the volume of said insertion tip.

8. The assembly as in claim 1, wherein said tapered tip occupies about 75% of the volume of said insertion tip.

9. The assembly as in claim 1, wherein said tapered tip occupies about 90% of the volume of said insertion tip.

10. The assembly as in claim 1, wherein said pledget comprises a material selected from the group consisting of rayon fibers, cotton fibers, pulp fibers, and any combinations thereof.

11. The assembly as in claim 1, wherein the taper ratio is linear along the entire extant of the length.

12. A tampon assembly comprising:
    a barrel having a tubular wall with a first end and a second end opposite said first end, said barrel having a plurality of discrete petals at said first end that define an insertion tip, said petals being separated from each other by a plurality of cuts that form a break of material through said tubular wall of said barrel, said insertion tip starting at a distal end of said first end and terminating at a first plane defined at a base of said plurality of petals, said insertion tip having a first taper ratio throughout its axial extant, said insertion tip having an inner surface area;
    a plunger being slidably received in said barrel; and
    a pledget having a front end and a rear end opposite said front end, said pledget having a tapered tip at said front end, said tapered tip having a taper so that an outer radial dimension of said tapered tip decreases between said front end of said pledget and a second plane through said pledget where said taper begins, said tapered tip having a second taper ratio that is equal to said first taper ratio, said pledget being disposed in said barrel so that said tapered tip contacts to support about 100% of said inner surface area of said insertion tip prior to insertion of the tampon assembly.

13. The assembly as in claim 12, wherein said insertion tip has a first taper ratio of more than about 0.3 to less than 1.0.

14. The assembly as in claim 12, wherein said pledget comprises a material selected from the group consisting of rayon fibers, cotton fibers, pulp fibers, and any combinations thereof.

15. The assembly as in claim 12, wherein said tapered tip has a density that is higher than or substantially equal to the density of the rest of said pledget.

* * * * *